United States Patent [19]
Jonishi et al.

[11] Patent Number: 5,869,683
[45] Date of Patent: Feb. 9, 1999

[54] PROCESSES FOR PRODUCING 1-SUBSTITUTED-2-CYANOIMIDAZOLE COMPOUNDS

[75] Inventors: Hisayoshi Jonishi; Tokiya Kimura; Fumio Kanamori; Shigehisa Kanbayashi; Tooru Wakabayashi; Fumihiro Fukui; Akimasa Takenaka; Noriyuki Horiuchi, all of Shiga, Japan

[73] Assignee: Ishihara Sangyo Kaisha, Ltd., Osaka, Japan

[21] Appl. No.: 962,648

[22] Filed: Nov. 3, 1997

Related U.S. Application Data

[63] Continuation of Ser. No. 524,767, Sep. 7, 1995, abandoned.

[30] Foreign Application Priority Data

Sep. 8, 1994 [JP] Japan .................................. 6-242164
Oct. 7, 1994 [JP] Japan .................................. 6-270321
Oct. 28, 1994 [JP] Japan .................................. 6-289267
Feb. 16, 1995 [JP] Japan .................................. 7-053629

[51] Int. Cl.$^6$ .................................................. C07D 233/90
[52] U.S. Cl. .......................................................... 548/337.1
[58] Field of Search .......................................... 548/337.1

[56] References Cited

U.S. PATENT DOCUMENTS 4,441,916 4/1984 Baker et al. ................................ 71/100
5,552,557 9/1996 Fuji et al. ............................. 548/337.1

FOREIGN PATENT DOCUMENTS 0 298 196 1/1989 European Pat. Off. .
0 337 103 10/1989 European Pat. Off. .

OTHER PUBLICATIONS

Crow and Hammond, "Organic Chemistry", McGraw–Hill Books, NY (1964) 2nd edition, pp. 565–567.
Chi–Tung et al, "Alpha–polyhaloacetone oxines", CA 106:66751 (1987).
Section Ch, Week 9215, Derwent Publications Ltd., London, GB; Class C02, An 92–118355 & JP–A–04 059 766 (Ishihara Sangyo Kaisha), Feb. 26, 1992.
Section Ch, Week 7705, Derwent Publications, Ltd., London, GB; Class C03, AN 77–08635Y & JP–B–52 000 019 (Bayer AG), Jan. 5, 1977.
"Methoden der Organischen, Chemie" Band E8c, Teil 3, Hetarene III; Jul. 7, 1994, pp. 7, 8, 21, 22, 51 and 52.
"Methoden der Organischen Chemie" Band E14b, Organische Stickstoff–Verbindungen mit einer C,N–Doppelbindung; Teil 1, 1990, pp. 316–318.

*Primary Examiner*—Patricia L. Morris
*Attorney, Agent, or Firm*—Sughrue, Mion, Zinn, Macpeak & Seas, PLLC

[57] ABSTRACT

A process for producing 1-substituted-2-cyanoimidazole compounds is described, which comprises (1) undergoing a reaction of a compound represented by formula (IV), hydroxylamine or a mineral acid salt thereof, and glyoxal or glyoxime to produce a compound represented by formula (III), (2) undergoing a reaction of the compound represented by formula (III) with thionyl chloride or thionyl bromide in the presence of N,N-dialkylamide to produce a reaction mixture, and then reacting the produced reaction mixture with sulfur chloride to produce a 2-cyanoimidazole compound represented by formula (II), and (3) undergoing a sulfamoylation reaction and an isomerization reaction of the 2-cyanoimidazole compound represented by formula (II) and a compound represented by formula (V) in the presence of at least one base selected from carbonates of alkali metals and bicarbonates of alkali metals and a polar solvent to produce a 1-substituted-2-cyanoimidazole compound represented by formula (I-b). The formulae and substituents formulae are specifically defined in the specification.

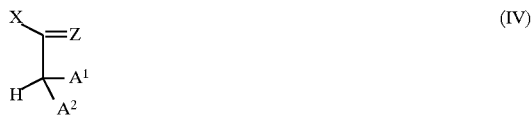

(IV)

5 Claims, No Drawings

PROCESSES FOR PRODUCING 1-SUBSTITUTED-2-CYANOIMIDAZOLE COMPOUNDS

This is a Continuation of application Ser. No. 08/524,767 filed Sep. 7, 1995, now abandoned.

FIELD OF THE INVENTION

The present invention relates to processes for producing 1-substituted-2-cyanoimidazole compounds useful as agricultural and horticultural fungicides.

BACKGROUND OF THE INVENTION

The 1-substituted-2-cyanoimidazole compounds are disclosed in EP-A-298196. Some methods for producing the 1-substituted-2-cyanoimidazole compounds have been proposed therein. However, none of these proposals include the processes of the present invention.

JP-A-4-59766 (The term "JP-A" as used herein means an "unexamined published Japanese patent application") discloses a process for producing 1-hydroxy-2-oxyiminomethylimidazole 3-oxide compounds as an intermediate. However, this process differs from process A of the present invention described below in that substituted glyoxal compounds are used as a starting material.

JP-A-4-59766 discloses a process for producing 2-cyanoimidazole compounds, which comprises reacting a 1-hydroxy-2-oxyiminomethylimidazole 3-oxide compound with a chloride or oxychloride of phosphorus or sulfur. However, JP-A-4-59766 does not disclose process B of the present invention described below producing 2-cyanoimidazole compounds represented by formula.(II) selectively and in a high yield.

EP-A-298196 discloses that (a) isomer mixtures of 1-substituted-2-cyanoimidazole compounds including compounds represented by formulae (I-a) and (I-b) of the present invention can be prepared by sulfamoylating 2-cyanoimidazole compounds represented by formula (II) of the present invention and that (b) the isomer mixtures can be separated by selective hydrolysis. Furthermore, JP-A-4-120063 discloses that only imidazole compounds represented by formula (I-b) of the present invention can be selectively separated from the isomer mixtures by using a solvent and an acid catalyst. However, EP-A-298196 and JP-A-4-120063 do not disclose process C of the present invention described below producing only imidazole compounds represented by formula (I-b) selectively by sulfamoylating and isomerizing the compounds represented by formula (II).

EP-A-298196 proposes some methods for producing 1-substituted-2-cyanoimidazole compounds. However, these methods are not satisfactory in their industrial application. Furthermore, it has been desired to produce 1-substituted-2-cyanoimidazole compounds more economically.

With regard to process A of the present invention, substituted glyoxal compounds used as a starting material in the process for producing 1-hydroxy-2-oxyiminomethylimidazole 3-oxide compounds are disclosed in JP-A-4-59766, but the industrial production of the substituted glyoxal compounds are difficult. JP-B-52-19 (The term "JP-B" as used herein means an "examined Japanese patent publication") discloses a process for producing substituted glyoxal compounds, which comprises reacting ketone and alkyl nitrite gas as starting materials in the presence of hydrogen halide. However, this process comprises a continuous reaction in which α-oxyimino ketone produced is extracted and removed and thus provides low productivity and requires a special apparatus.

With regard to process B of the present invention, in the process for producing 2-cyanoimidazole compounds disclosed in JP-A-4-59766, the chloride or oxychloride of phosphorus or sulfur for use in the reaction of the process is preferably phosphorus trichloride. When phosphorus oxychloride, phosphorus monochloride, sulfur monochloride, sulfur dichloride, thionyl chloride or sulfuryl chloride is used, the reduction reaction may be incomplete under some conditions. This production process is also disadvantageous in that the use of phosphorus trichloride requires much labor and facilities for the disposal of waste water after reaction. The reaction of phosphorus trichloride is further disadvantageous in that it has an induction period, making it difficult to control the reaction temperature. This preparation process is further disadvantageous in that the resulting compound contains a compound that is not chlorinated in the 4- or 5-position on the imidazole ring. Thus, a separate chlorination step is required to obtain a compound that is chlorinated at the 4- or 5-position on the imidazole ring.

With regard to process C of the present invention, in the process for selectively separating and collecting compounds represented by formula (I-b) from isomer mixtures of 1-substituted-2-cyanoimidazole compounds disclosed in EP-A-298196 and JP-A-4-120063, compounds represented by formula (I-a) are hydrolyzed and the process is thus disadvantageous in that its yield does not exceed the ratio of the isomers of the compounds represented by formula (I-b) and that the post-treatment is complicated.

SUMMARY OF THE INVENTION

An object of the present invention is to provide a process for producing 1-substituted-2-cyanoimidazole compounds without using any substituted glyoxal compound as a starting material.

Another object of the present invention is to provide a process for producing 1-substituted-2-cyanoimidazole compounds free from the problems of disposal of phosphorus-containing waste water and control over the reaction temperature.

A further object of the present invention is to provide a process for producing 1-substituted-2-cyanoimidazole compounds without employing selective hydrolysis.

A still further object of the present invention is to enhance the proportion of isomers of the desired compound represented by formula (I-b) described below.

The inventors made extensive studies on the objects. As a result, the following knowledge was obtained:

1) a compound represented by formula (IV) described below can be used as a starting material;
2) thionyl chloride and sulfur chloride can be used in two stage reactions instead of phosphorus trichloride to produce 2-cyanoimidazole compounds selectively and in a high yield; and
3) an isomerization reaction can provide 1-substituted-2-cyanoimidazole compounds represented by formula (I-b) as the desired compound selectively and in a high yield. Thus, the present invention has been worked out.

These and other objects of the present invention have been achieved by a process for producing l-substituted-2-cyanoimidazole compounds, which comprises (1) undergoing a reaction of a compound represented by the following formula (IV), hydroxylamine or a mineral acid salt thereof, and glyoxal or glyoxime to produce a compound represented by the following formula (III):

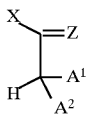

(IV)

wherein $A^1$ represents a hydrogen atom, a chlorine atom or a bromine atom; $A^2$ represents a chlorine atom or a bromine atom; X represents a phenyl group which may be substituted or an alkyl group which may be substituted; and Z represents an oxygen atom or a hydroxyimino group:

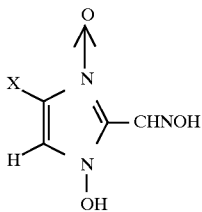

(III)

wherein X has the same meaning as defined above, (2) undergoing a reaction of the compound represented by formula (III) with thionyl chloride or thionyl bromide in the presence of N,N-dialkylamide to produce a reaction mixture, and then undergoing a reaction of the reaction mixture with sulfur chloride to produce a 2-cyanoimidazole compound represented by the following formula (II):

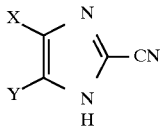

(II)

wherein X has the same meaning as defined above; and Y represents a chlorine atom or a bromine atom, and (3) undergoing a sulfamoylation reaction and an isomerization reaction of the 2-cyanoimidazole compound represented by formula (II) and a compound represented by the following formula (V) in the presence of at least one base selected from the group of consisting of carbonates of alkali metals and bicarbonates of alkali metals and a polar solvent to produce a 1-substituted-2-cyanoimidazole compound represented by the following formula (I-b):

Hal—SO$_2$N(R$^1$)R$^2$ (V)

wherein Hal represents a halogen atom; and $R^1$ and $R^2$ each represents an alkyl group:

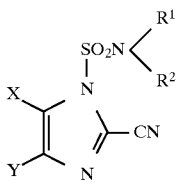

(I-b)

wherein $R^1$, $R^2$, X and Y each has the same meaning as defined above (herein referred to as "process D" of the present invention).

Furthermore, these and other objects of the present invention have been achieved by a process for producing compounds represented by the following formula (III), which comprises undergoing a reaction of a compound represented by the following formula (IV), hydroxylamine or a mineral acid salt thereof, and glyoxal or glyoxime:

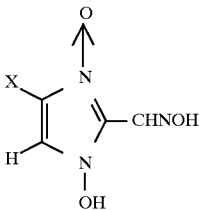

(III)

wherein X represents a phenyl group which may be substituted or an alkyl group which may be substituted;

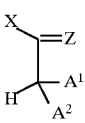

(IV)

wherein $A^1$ represents a hydrogen atom, a chlorine atom or a bromine atom; $A^2$ represents a chlorine atom or a bromine atom; X has the same meaning as defined above; and Z represents an oxygen atom or a hydroxyimino group (herein referred to as "process A" of the present invention).

Moreover, these and other objects of the present invention have been achieved by a process for producing 2-cyanoimidazole compounds represented by the following formula (II), which comprises undergoing a reaction of a compound represented by the following formula (III) with thionyl chloride or thionyl bromide in the presence of N,N-dialkylamide to produce a reaction mixture, and then undergoing a reaction of the reaction mixture with sulfur chloride:

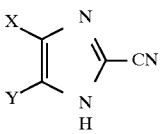

(II)

wherein X represents a phenyl group which may be substituted or an alkyl group which may be substituted; and Y represents a chlorine atom or a bromine atom:

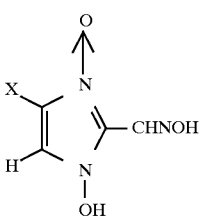

(III)

wherein X has the same meaning as defined above (herein referred to as "process B" of the present invention).

In addition, these and other objects of the present invention have been achieved by a process for producing 1-substituted-2-cyanoimidazole compounds represented by the following formula (I-b), which comprises undergoing a sulfamoylation reaction and an isomerization reaction of a compound represented by the following formula (II) and a compound represented by the following formula (V) in the presence of at least one base selected from carbonates of alkali metals and bicarbonates of alkali metals and a polar solvent:

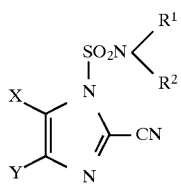

(I-b)

wherein $R^1$ and $R^2$ each represents an alkyl group; X represents a phenyl group which may be substituted or an alkyl group which may be substituted; and Y represents a chlorine atom or a bromine atom;

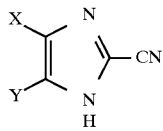

(II)

wherein X and Y each has the same meaning as defined above;

(V)

wherein Hal represents a halogen atom; and $R^1$ and $R^2$ each has the same meaning as defined above (herein referred to as "process C" of the present invention).

DETAILED DESCRIPTION OF THE INVENTION

Examples of substituents on the phenyl group which may be substituted represented by X include halogen atoms (e.g., fluorine, chlorine, bromine, iodine), $C_{1-3}$ alkyl groups (e.g., methyl, ethyl, propyl), and $C_{1-3}$ alkoxy groups (e.g., methoxy, ethoxy, propoxy). The number of the substituents on the phenyl group is from 1 to 5. If there are two or more substituents, they may be the same or different. Examples of substituents on the alkyl group which may be substituted represented by X include halogen atoms (e.g., fluorine, chlorine), a phenyl group, and $C_{1-3}$ alkoxy groups. The number of the substituents on the alkyl group is one or more. If there are two or more substituents, they may be the same or different. The alkyl moiety of the alkyl group which may be substituted represented by X include $C_{1-8}$ straight-chain or branched alkyl groups. Examples thereof include a methyl group, an ethyl group, a propyl group, a butyl group, a pentyl group, a hexyl group, a heptyl group, and an octyl group.

Specific examples of the groups represented by X include a phenyl group; a 2-, 3- or 4-fluorophenyl group; a 2-, 3- or 4-chlorophenyl group; a 2-, 3- or 4-bromophenyl group; a 2-, 3- or 4-methylphenyl group; a 2-, 3- or 4-ethylphenyl group; a 2-, 3- or 4-propylphenyl group; a 2-, 3- or 4-methoxyphenyl group; a 2-, 3- or 4-ethoxyphenyl group; a 3,4-dichlorophenyl group; a 3,4-dimethylphenyl group; a 3,4-dimethoxyphenyl group; a 3-methyl-4-methoxyphenyl group; a 3-chloro-4-methylphenyl group; a 3-chloro-4-methoxyphenyl group; a tert-butyl group; and a 1,1-dimethylpropyl group.

The alkyl group represented by $R^1$ or $R^2$ include $C_{1-2}$ alkyl groups. Examples of the $C_{1-2}$ alkyl groups include a methyl group, an ethyl group, a propyl group, an isopropyl group, a butyl group, a sec-butyl group, an isobutyl group, a tert-butyl group, a pentyl group, a hexyl group, a heptyl group, an octyl group, a nonyl group, and a decyl group. Among these, $R^1$ and $R^2$ are each preferably a methyl group. Examples of the halogen atom represented by Hal include a chlorine atom, a bromine atom, and an iodine atom. Among these, Hal is preferably a chlorine atom.

In the first step (1) of process D of the present invention or in process A of the present invention, a compound represented by formula (IV) reacts with hydroxylamine or a mineral acid salt thereof, and glyoxal or glyoxime to produce a compound represented by formula (III) that is a starting material in the second step (2) of process D of the present invention or in process B of the present invention.

Specific examples of the compounds represented by formula (IV) include 2,2-dichloroacetophenone, 2,2,4'-trichloroacetophenone, 4'-bromo-2,2-dichloroacetophenone, 2-chloro-4'-methylacetophenone,2-chloro-4'-methylacetophenone oxime, 2-bromo-4'-methylacetophenone, 2-bromo-4'-methylacetophenone oxime, 2,2-dichloro-4'-methylacetophenone, 2,2-dichloro-4'-methylacetophenoneoxime, 2-bromo-2-chloro-4'-methylacetophenone, 2-bromo-2-chloro-4'-methylacetophenone oxime, 2,2-dibromo-4'-methylacetophenone, 2,2-dibromo-4'-methylacetophenone oxime, 2,2-dichloro-4'-ethylacetophenone, 2,2-dichloro-4'-methoxyacetophenone, 1,1-dichloro-3,3-dimethyl-2-butanone, 1,1-dibromo-3,3-dimethyl-2-butanone, 1,1-dichloro-3,3-dimethyl-2-pentanone, and 1,1-dibromo-3,3-dimethyl-2-pentanone. Among these, 2,2-dichloro-4'-methylacetophenone oxime, 2-bromo-2-chloro-4'-methylacetophenone oxime, and 2,2-dibromo-4'-methylacetophenone oxime are novel compounds.

Examples of the mineral acid salt of hydroxylamine include hydroxylamine hydrochloride, hydroxylamine hydrobromide, and hydroxylamine sulfate.

Among the compounds represented by formula (IV), compound (IV-1) in which Z is an oxygen atom reacts with a mineral acid salt of hydroxylamine to produce compound (IV-2) in which Z is a hydroxylimino group.

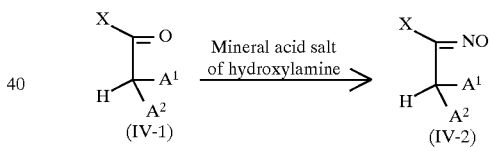

The compound in which Z is a hydroxylimino group has geometrical isomers because its double bond.

Furthermore, glyoxal reacts with a mineral acid salt of hydroxylamine to produce glyoxime.

In the process for producing the compound represented by formula (III) from the compound represented by formula (IV), the amount added of the hydroxylamine or mineral acid salt thereof is usually from 1 to 8 equivalents per mol of the compound represented by formula (IV). If the glyoxal is used in combination, the amount added of the hydroxylamine or mineral acid salt thereof is from 3 to 8 equivalents, preferably from 3.5 to 6.0 equivalents, per mol of the compound represented by formula (IV). If the glyoxime is used in combination, the amount added of the hydroxylamine or mineral acid salt thereof is from 1 to 6 equivalents, preferably from 1.5 to 4.0 equivalents, per mol of the compound represented by formula (IV).

The amount added of the glyoxal or glyoxime is usually from 0.5 to 2.0 mol, preferably from 0.8 to 1;6 mol, per mol of the compound represented by formula (IV).

In the process of the present invention, a solvent is preferably used. Any solvent can be used as long as the solvent has no adverse effects on the reactions. Examples of the solvent for use in the present invention include water, alcohols (e.g., methanol, ethanol, propanol), and organic acids (e.g., formic acid, acetic acid). These solvents may be used singly or in combination. Particularly, water or alcohol is preferably used. The amount added of the solvents is from 1 to 20 parts by weight, preferably from 2 to 6 parts by weight, based on one part by weight of the compound represented by formula (IV).

In the reaction, the reaction temperature is from 30° C. to 120° C., preferably from 60° C. to 100° C.; and the reaction time is from 1 to 40 hours.

In the process of the present invention, the compound represented by formula (III) may be provided by reacting the compound represented by formula (IV-1) with a mineral acid salt of hydroxylamine to produce a compound represented by formula (IV-2) as a first reaction and then reacting the compound represented by formula (IV-2) with glyoxal or glyoxime in the presence or absence of a mineral acid salt of hydroxylamine as a second reaction.

The first reaction is an oximization reaction. The amount of the mineral acid salt of hydroxylamine in the oximization reaction is usually from 1 to 4 equivalents, preferably from 2 to 3.5 equivalents, per mol of the compound represented by formula (IV-1). The reaction temperature is from 30° C. to 100° C., preferably from 60° C. to 90° C. The reaction time is from 0.2 to 10 hours.

The second reaction is a cyclization reaction. The amount added of the mineral acid salt of hydroxylamine in the cyclization reaction is usually from 0 to 6 equivalents per mol of the compound represented by formula (IV-2). If the glyoxal is used in combination, the amount added of the mineral acid salt of hydroxylamine is from 2 to 6 equivalents, preferably from 3 to 4 equivalents, per mol of the compound represented by formula (IV-2). If the glyoxime is used in combination, the amount added of the mineral acid salt of hydroxylamine is from 0 to 4 equivalents, preferably from 1 to 2 equivalents, per mol of the compound represented by formula (IV-2). If the mineral acid salt of hydroxylamine is not used, the cyclization reaction may be carried out by adding a mineral acid to the reaction system. The amount added of the glyoxal or glyoxime in the cyclization reaction is usually from 0.5 to 2.0 mol, preferably from 0.8 to 1.6 mol, per mol of the compound represented by formula (IV-2). The reaction temperature is from 50° C. to 120° C., preferably from 60° C. to 100° C. The reaction time is from 0.8 to 30 hours.

In this oximization reaction, a compound represented by formula (VI) described below may be produced as a by-product besides the compound represented by formula (IV-2) on some conditions.

Alternatively, in the process of the present invention, a compound represented by formula (III) may be provided by reacting a compound represented by the following formula (IV-1') with hydroxylamine to produce a compound represented by formula (VI) as a first reaction and then reacting the compound represented by formula (VI) with glyoxal or glyoxime in the presence or absence of a mineral acid salt of hydroxylamine as a second reaction:

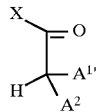
(IV-1')

wherein X and AZ each has the same meaning as defined above; and $A^1$ represents a chlorine atom or a bromine atom:

wherein X has the same meaning as defined above.

The first reaction is an oximization reaction. The amount added of the hydroxylamine in the oximization reaction is usually from 2 to 6 equivalents, preferably from 3 to 5 equivalents, per mol of the compound represented by formula (IV-1'). The excessive amount of the hydroxylamine may form hydroxylamine hydrochloride or hydroxylamine hydrobromide with HCl or HBr produced as a by-product. The hydroxylamine hydrochloride or hydroxylamine hydrobromide thus produced can be used as a mineral acid salt of hydroxylamine in the second reaction. If the hydroxylamine is not used in excess, a base may be added to the reaction system. The reaction temperature is from 30° C. to 100° C., preferably from 60° C. to 90° C. The reaction time is from 0.2 to 10 hours.

Specific examples of the compound represented by formula (VI) produced by the oximization reaction include phenylglyoxime, 4-chlorophenylglyoxime, 4-bromophenylglyoxime, 4-methylphenylglyoxime, 4-ethylphenylglyoxime, 4-methoxyphenylglyoxime, 3,3-dimethyl-1,2-butanedione dioxime, and 3,3-dimethyl-1,2-pentanedione dioxime.

The second reaction is a cyclization reaction. The amount added of the mineral acid salt of hydroxylamine in the cyclization reaction is usually from 0 to 4 equivalents per mol of the compound represented by formula (VI). If glyoxal is used in combination, the amount added of the mineral acid salt of hydroxylamine is from 1 to 4 equivalents, preferably from 2 to 3 equivalents. If glyoxime is used in combination, the amount added of the mineral acid salt of hydroxylamine is from 0 to 2 equivalents, preferably from 0.5 to 1 equivalent. If the mineral acid salt of hydroxylamine is not used, the cyclization reaction may be carried out by adding a mineral acid to the reaction system. Examples of the mineral acid include hydrochloric acid, sulfuric acid and hydrobromic acid. The amount added of the glyoxal or glyoxime in the reaction is usually from 0.5 to 2.0 mol, preferably from 0.8 to 1.6 mol, per mol of the compound represented by formula (VI). The reaction temperature is from 50° C. to 120° C., preferably from 60° C. to 100° C. The reaction time is from 0.8 to 30 hours.

The compound represented by formula (IV-1) or (IV-1') belonging to formula (IV) can be prepared by reacting a compound represented by the following formula (VII) with chlorine or bromine:

wherein X has the same meaning as defined above. After the compound represented by formula (IV-1) or (IV-1') is produced, the compound represented by formula (III) can be produced without any separation and purification processing.

Specific examples of the compound represented by formula (VII) include acetophenone, 4'-chloroacetophenone, 4'-bromoacetophenone, 4'-methylacetophenone, 4'-ethylacetophenone, 4'-methoxyacetophenone, 3,3-dimethyl-2-butanone, and 3,3-dimethyl-2-pentanone. The amount added of the chlorine or bromine in the reaction is usually from 0.8 to 4 mol per mol of the compound represented by formula (VII). The reaction temperature is usually from 0° C. to 100° C. If the chlorine is used, the reaction temperature is from 20° C. to 100° C. If the bromine is used, the reaction temperature is from 0° C. to 80° C. The reaction time depends on the rate of introduction of the chlorine or bromine and thus cannot be unconditionally defined.

However, the reaction time is usually from 0.5 to 30 hours. This reaction may be carried out in the presence of a solvent. Examples of the solvent include alcohols (e.g., methanol, ethanol, propanol), and organic acids (e.g., formic acid, acetic acid). If the melting points of the starting material and the reaction product are 80° C. or less, the reaction may be carried out without a solvent. In the process of the present invention, the thus produced compound represented by formula (IV-1) or (IV-1') belonging to formula (IV) reacts with hydroxylamine or a mineral acid salt thereof, and glyoxal or glyoxime. For continuance of the two reactions, the first reaction, i.e., reaction of the compound represented by formula (VII) with chlorine or bromine, is preferably carried out without a solvent or in the presence of the same solvent as used in the subsequent reaction, more preferably without a solvent.

The second step (2) of process D of the present invention and process B of the present invention consist of two reactions, i.e., a first reaction, in which a compound represented by formula (III) reacts with thionyl chloride or thionyl bromide in the presence of N,N-dialkylamide, and a second reaction, in which the reaction product of the first reaction reacts with sulfur chloride.

The amount added of the thionyl chloride or thionyl bromide in the first reaction is from 1 to 5 mol, preferably from 1.5 to 3 mol, per mol of the compound represented by formula (III).

The first reaction is carried out in the presence of N,N-dialkylamide as a solvent. Examples of the N,N-dialkylamide include dimethylformamide, dimethylacetamide, and N-methylpyrrolidone. The amount added of the N,N-dialkylamide is from 0.5 to 10 l, preferably from 1.5 to 5 l, per kg of the compound represented by formula (III). The N,N-dialkylamides can be used in combination with an aprotic solvent. Examples of the aprotic solvent include halogenated hydrocarbons (e.g., methylene chloride, chloroform, carbon tetrachloride, 1,2-dichloroethane), ethers (e.g., diethyl ether, dipropyl ether, tetrahydrofuran, 1,4-dioxane), ketones (e.g., acetone, methyl ethyl ketone, methyl isobutyl ketone), nitriles (e.g., acetonitrile, propionitrile, benzonitrile), esters (e.g., ethyl acetate, methyl acetate), and aromatic hydrocarbons (e.g., benzene, toluene, xylene, chlorobenzene).

In this first reaction, the reaction temperature is from −10° C. to +80° C., preferably from 0° C. to 50° C.; and the reaction time is from 0.1 to 10 hours.

The main product of the reaction comprises a 2-cyanoimidazole compound represented by formula (II) and a compound represented by the following formula (II'):

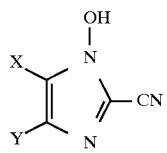

wherein X has the same meaning as defined above. The reaction may produce a small amount of a compound represented by the following formula (VIII):

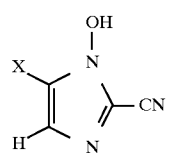

wherein X has the same meaning as defined above. The first reaction may be followed by an ordinary post-treatment, e.g., a process which comprises putting the reaction mixture into ice water, extracting the reaction mixture with an organic solvent such as methylene chloride, distilling off the extract, and then separating the extract by silica gel chromatography, to obtain the products. However, for production of the desired 2-cyanoimidazole compound represented by formula (II) selectively and in a high yield, it is preferred that the first reaction be directly followed by the second reaction without any post-treatment. On the other hand, if the thionyl chloride or thionyl bromide is used in excess per the compound represented by formula (III) in the first reaction, by-products can be easily produced under some reaction conditions. In this case, the production of these by-products can be inhibited by adding lower alcohol to the reaction mixture after the reaction. $C_{1-3}$ alcohol (e.g., methanol, ethanol, propanol) is preferably used as the lower alcohol. The amount added of the lower alcohol depends on the amount added of the thionyl chloride or thionyl bromide and other reaction conditions, but is usually from 0.5 to 2 mol per mol of the compound represented by formula (III).

Examples of the sulfur chloride for use in the second reaction include sulfur monochloride and sulfur dichloride. These sulfur chlorides may be used singly or in combination. The amount added of the sulfur chloride is from 0.5 to 5 mol, preferably from 0.7 to 3 mol, per mol of the compound represented by formula (III).

The reaction is carried out in the presence of a solvent. Examples of the solvent for use in the reaction include the above-described N,N-dialkylamides and aprotic solvents. If the first reaction is directly followed by the second reaction without any post-treatment, the solvent used in the first reaction can be used as it is in the second reaction.

In this second reaction, the reaction temperature is from −10° C. to +80° C., preferably from 0° C. to 50° C.; and the reaction time is from 0.1 to 10 hours.

The reaction may be followed by an ordinary post-treatment, e.g., a process which comprises putting the reaction mixture into ice water, recovering the resulting crystal by filtration, washing the crystal thus recovered, and then drying the crystal, to obtain the desired product.

The compound represented by formula (II) has the following tautomers:

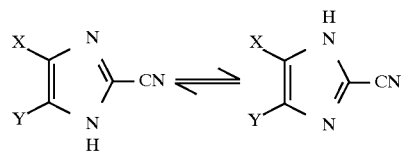

The 2-cyanoimidazole compounds represented by formula (II) can be converted to the 1-substituted-2-cyanoimidazole compounds disclosed in EP-A-298196 by an ordinary sulfamoylation reaction or by a sulfamoylation and an isomerization according to the third step (3) of process D of the present invention or according to process C of the present invention. The 1-substituted-2-cyanoimidazole compounds thus produced can be used as agricultural and horticultural fungicides.

In accordance with the third step (3) in process D of the present invention or with process C of the present invention, a sulfamoylation reaction and an isomerization reaction are carried out between a compound represented by formula (II) and a compound represented by formula (V) in the presence of a specific base and a polar solvent.

Since the compounds represented by formula (II) have tautomers, the progress of the sulfamoylation reaction of the compounds represented by formula (II) produces a compound represented by the following formula (I-a) besides a compound represented by formula (I-b) in the progressing reaction system:

(I-a)

wherein $R^1$, $R^2$, X and Y each has the same meaning as defined above.

Therefore, the third step (3) of process D of the present invention and process C of the present invention comprise undergoing a sulfamoylation reaction of the compound represented by formula (II) and at the same time an isomerization reaction, which isomerizes the produced compound represented by formula (I-a) to a compound represented by formula (I-b), in the presence of at least one base selected from carbonates of alkali metals and bicarbonates of alkali metals and a polar solvent.

For progress of the sulfamoylation reaction and the isomerization reaction, the compound represented by formula (V) is preferably used in an amount of from 1.1 to 2.1 mol per mol of the compound represented by formula (II). For production of only compound represented by formula (I-b) in a high yield, the compound represented by formula (V) is preferably added batchwise two or more times during the reaction. Examples of the batchwise addition process include various processes such as dropwise addition. In a preferred embodiment of the process, the compound represented by formula (V) is first added in an amount of from 1.0 to 1.6 mol per mol of the compound represented by formula (II). When the reaction is completed or toward the end of the reaction, the remaining amount (from 0.1 to 0.5 mol) of the compound represented by formula (V) may be added to the reaction system.

The base for use in the reaction is at least one selected from carbonates of alkali metals and bicarbonates of alkali metals. Examples thereof include carbonates of alkali metals (e.g., potassium carbonate, sodium carbonate), and bicarbonates of alkali metals (e.g., potassium bicarbonate, sodium bicarbonate). Among these, carbonates of alkali metals are preferred, and potassium carbonate is particularly preferred.

For progress of the sulfamoylation reaction and the isomerization reaction in the process of the present invention, a base is preferably used in an amount of from 0.75 to 2.1 equivalents per mol of the compound represented by formula (II). For production of only compound represented by formula (I-b) in a high yield, the base is preferably added batchwise two or more times during the reaction. Examples of the batchwise addition process include various processes. In a preferred embodiment, the base is first added in an amount of from 0.65 to 1.6 equivalents per mol of the compound represented by formula (II). When the reaction is completed or toward the end of the reaction, the remaining amount (from 0.1 to 0.5 equivalents) of the base may be added.

Examples of the polar solvent for use in this process may be any polar solvent capable of dissolving the compound represented by formula (I-a) or (I-b) therein. Examples of the polar solvent include ketones (e.g., acetone, methyl ethyl ketone, methyl isobutyl ketone), nitrites (e.g., acetonitrile, propionitrile), aprotic polar solvents (e.g., dimethylformamide, N-methylpyrrolidone, dimethyl sulfoxide, sulfolane), alcohols (e.g., methanol, ethanol, propanol, butanol), and esters (e.g., ethyl acetate, methyl acetate). Among these, methyl ethyl ketone and ethyl acetate are preferred. The amount added of the polar solvent in this process is usually from 1 to 3 l, preferably from 1.5 to 2 l, per kg of the compound represented by formula (II).

In this process, the sulfamoylation reaction and the isomerization reaction are preferably carried out while the polar solvent is gradually distilled off. If the base and/or the compound represented by formula (V) is batchwise added for the reaction, the polar solvent is preferably distilled off after the batchwise addition.

In this process, the reaction temperature of the sulfamoylation reaction and the isomerization reaction is preferably from 20° C. to 110° C. If the base and/or the compound represented by formula (V) is batchwise added for the reaction, the reaction temperature before the batchwise addition of these components is from 20° C. to 110° C., preferably from 60° C. to 100° C., and the reaction temperature after the batchwise addition of these components is from 20° C. to 110° C., preferably from 60° C. to 100° C. More preferably, the reaction temperatures before and after the batchwise additions are each from 65° C. to 85° C.

The present invention will be further described in the following examples, but the present invention should not be construed as being limited thereto.

EXAMPLE 1

Into a 200-ml four-necked flask equipped with a thermometer, a condenser and an agitator were charged 10.15 g of 2,2-dichloro-4'-methylacetophenone, 7.98 g of a 40% aqueous solution of glyoxal, 16.4 g of hydroxylamine sulfate and 30 ml of methanol. The reaction mixture was then stirred under reflux for 24 hours.

After the completion of the reaction, the reaction mixture was cooled to room temperature. Then, 60 ml of water was poured into the reaction mixture. The reaction mixture was then stirred for 20 minutes. The resulting crystal was recovered by filtration, and then dried to obtain 10.48 g of a crude crystal of 1-hydroxy-4(5)-(4-methylphenyl)-2-oxyiminomethylimidazole 3-oxide. The crude crystal thus obtained was dispersed in 20 ml of methanol, recovered by filtration, washed with methanol, and then dried to obtain 9.49 g of a purified crystal (m.p. 225°–228° C. (decomposition)).

EXAMPLE 2

Into a 200-ml four-necked flask equipped with a thermometer, a condenser and an agitator were charged 15.0 g of 4'-bromo-2,2-dichloroacetophenone, 8.9 g of a 40% aqueous solution of glyoxal, 27.6 g of hydroxylamine sulfate and 45 ml of methanol. The reaction mixture was then stirred under reflux for 13 hours.

After the completion of the reaction, the reaction mixture was cooled to room temperature. Then, 90 ml of water was poured into the reaction mixture. The reaction mixture was then stirred for 20 minutes. The resulting crystal was recovered by filtration, and then dried to obtain 15.3 g of a crude crystal of 4(5)-(4-bromophenyl)-1-hydroxy-2- oxyiminomethylimidazole 3-oxide. The crude crystal thus obtained was dispersed in 30 ml of methanol, recovered by filtration, washed with methanol, and then dried to obtain 12.18 g of a purified crystal (m.p. 231°–238° C. (decomposition)).

EXAMPLE 3

Into a 100-ml four-necked flask equipped with a thermometer, a condenser and an agitator were charged 5.08 g of 2,2-dichloro-4'-methylacetophenone, 2.48 g of glyoxime, 4.5 g of hydroxylamine sulfate and 25 ml of methanol. The reaction mixture was then stirred under reflux for 28 hours.

After the completion of the reaction, the reaction mixture was cooled to room temperature. Then, 50 ml of water was poured into the reaction mixture. The reaction mixture was then stirred for 20 minutes. The resulting crystal was recovered by filtration, and then dried to obtain 5.23 g of a crude crystal of 1-hydroxy-4(5)-(4-methylphenyl)-2-oxyiminomethylimidazole 3-oxide. The crude crystal thus obtained was dispersed in 15 ml of methanol, recovered by filtration, washed with methanol, and then dried to obtain 4.50 g of a purified crystal.

EXAMPLE 4

Into a 100-ml four-necked flask equipped with a thermometer, a condenser and an agitator were charged 5.33 g of 2-bromo-4'-methylacetophenone, 2.4 g of glyoxime, 4.5 g of hydroxylamine sulfate and 15 ml of methanol. The reaction mixture was then stirred under reflux for 15 hours.

After the completion of the reaction, the reaction mixture was cooled to room temperature. Then, 30 ml of water was poured into the reaction mixture. The reaction mixture was then stirred for 20 minutes. The resulting crystal was recovered by filtration, and then dried to obtain 5.29 g of a crude crystal of 1-hydroxy-4(5)-(4-methylphenyl)-2-oxyiminomethylimidazole 3-oxide. The crude crystal thus obtained was dispersed in 15 ml of methanol, recovered by filtration, washed with methanol, and then dried to obtain 4.56 g of a purified crystal.

EXAMPLE 5

Into a 100-ml four-necked flask equipped with a thermometer, a condenser and an agitator were charged 5.0 g of 2,2-dibromo-4'-methylacetophenone, 2.7 g of glyoxime, 7.0 g of hydroxylamine sulfate and 25 ml of methanol. The reaction mixture was then stirred under reflux for 10 hours.

After the completion of the reaction, the reaction mixture was cooled to room temperature. Then, 50 ml of water was poured into the reaction mixture. The reaction mixture was then stirred for 20 minutes. The resulting crystal was recovered by filtration, and then dried to obtain 3.65 g of a crude crystal of 1-hydroxy-4(5)-(4-methylphenyl)-2-oxyiminomethylimidazole 3-oxide. The crude crystal thus obtained was dispersed in 10 ml of methanol, recovered by filtration, washed with methanol, and then dried to obtain 2.74 g of a purified crystal.

EXAMPLE 6

Into a 300-ml four-necked flask equipped with a thermometer, a condenser and an agitator was charged 13.4 g of 4'-methylacetophenone. Chlorine gas was then introduced into the reaction mixture at a temperature of from 50° C. to 60° C. After the conversion of 4'-methylacetophenone to 2,2-dichloro-4'-methylacetophenone was identified by gas chromatography, 17.4 g of a 40% aqueous solution of glyoxal, 36.1 g of hydroxylamine sulfate and 70 ml of methanol were added to the reaction system. The reaction mixture was then stirred under reflux for 18 hours.

After the completion of the reaction, the reaction mixture was cooled to room temperature. Then, 140 ml of water was poured into the reaction mixture. The reaction mixture was then stirred for 20 minutes. The resulting crystal was recovered by filtration, and then dried to obtain 20.1 g of a crude crystal of 1-hydroxy-4(5)-(4-methylphenyl)-2-oxyiminomethylimidazole 3-oxide. The crude crystal thus obtained was dispersed in 50 ml of methanol, recovered by filtration, washed with methanol, and then dried to obtain 17.83 g of a purified crystal.

EXAMPLE 7

Into a 300-ml four-necked flask equipped with a thermometer, a condenser and an agitator were charged 20.3 g of 2,2-dichloro-4'-methylacetophenone, 20.9 g of hydroxylamine hydrochloride and 200 ml of methanol. The reaction mixture was then stirred at room temperature for 3 days.

The reaction mixture was then poured into 600 ml of water, and then extracted with methylene chloride. The solvent was then distilled off to obtain 20.8 g of a mixture of isomers of 2,2-dichloro-4'-methylacetophenone oxime (syn/anti=1/1). The mixture was partially sampled, washed with hexane, and then measured for the melting point of one of the isomers. The result was 100° C. to 104° C.

EXAMPLE 8

Into a 200-ml four-necked flask equipped with a thermometer, a condenser and an agitator were charged 10.0 g of the mixture of isomers of 2,2-dichloro-4'-methylacetophenone oxime obtained in Example 7, 7.14 g of a 40% aqueous solution of glyoxal, 13.3 g of hydroxylamine sulfate and 30 ml of methanol. The reaction mixture was then stirred under reflux for 16 hours.

After the completion of the reaction, the reaction mixture was cooled to room temperature. Then, 60 ml of water was poured into the reaction mixture. The reaction mixture was then stirred for 20 minutes. The resulting crystal was recovered by filtration, and then dried to obtain 9.62 g of a crude crystal of 1-hydroxy-4(5)-(4-methylphenyl)-2-oxyiminomethylimidazole 3-oxide. The crude crystal thus obtained was dispersed in 30 ml of methanol, recovered by filtration, washed with methanol, and then dried to obtain 8.43 g of a purified crystal.

EXAMPLE 9

Into a 100-ml four-necked flask equipped with a thermometer, a condenser, an agitator and a dropping funnel were charged 4.06 g of 2,2-dichloro-4'-methylacetophenone and 6.6 g of a 50% aqueous solution of hydroxylamine. The reaction mixture was then stirred at a temperature of 90° C. for about one hour to produce 4-methylphenylglyoxime (m.p. 170°–176° C.). To the product was then added 3.19 g of a 40% aqueous solution of glyoxal. The reaction mixture was then kept at a temperature of 90° C. for about one hour.

After the completion of the reaction, the resulting crystal was recovered by filtration, washed with water, and then dried to obtain 3.96 g of 1-hydroxy-4(5)-(4-methylphenyl)-2-oxyiminomethylimidazole 3-oxide.

EXAMPLE 10

Into a 100-mL four-necked flask equipped with a thermometer, a condenser, an agitator and a dropping funnel were charged 4.06 g of 2,2-dichloro-4'-methylacetophenone, 5.28 g of a 50% aqueous solution of hydroxylamine and 8 ml of methanol. The reaction mixture was then kept under reflux for about one hour to produce 4-methylphenylglyoxime. Methanol was then distilled off from the reaction system. To the reaction system was then added 2.9 g of a 40% aqueous solution of glyoxal. The reaction mixture was then kept at a temperature of 90° C. for about 2.5 hours.

After the completion of the reaction, the resulting crystal was recovered by filtration, washed with water, and then dried to obtain 4.16 g of 1-hydroxy-4(5)-(4-methylphenyl)-2-oxyiminomethylimidazole 3-oxide.

EXAMPLE 11

Into a 100-ml four-necked flask equipped with a thermometer, a condenser, an agitator and a dropping funnel were sequentially charged 10.8 g of a 44.4% aqueous solution of sodium hydroxide, 9.84 g of hydroxylamine sulfate, 6.09 g of 2,2-dichloro-4'-methylacetophenone and 6 ml of methanol. The reaction mixture was then kept under reflux for about 3 hours to produce 4-methylphenylglyoxime. To the product were then added 4.35 g of a 40% aqueous solution of glyoxal, 6 ml of water and 2.94 g of sulfuric acid. The reaction mixture was then kept at a temperature of 80° C. for about 5 hours.

After the completion of the reaction, the resulting crystal was recovered by filtration, washed with water, and then dried to obtain 5.94 g of 1-hydroxy-4(5)-.(4-methylphenyl)-2-oxyiminomethylimidazole 3-oxide.

EXAMPLE 12

Into a 100-ml four-necked flask equipped with a thermometer, a condenser, an agitator and a dropping funnel were charged 11.65 g of 1-hydroxy-4(5)-(4-methylphenyl)-2-oxyiminomethylimidazole 3-oxide and 35 ml of dimethylformamide. To the reaction mixture was then added dropwise 11.9 g of thionyl chloride with stirring while cooling the reaction system to 25° C. or less. The reaction mixture was then further stirred at room temperature for about one hour. After cooling the reaction system again to about 10° C., 7.73 g of sulfur dichloride was added dropwise to the reaction mixture. The reaction mixture was then stirred for about one hour.

The reaction mixture was then gradually added dropwise to 200 ml of ice water. The reaction mixture was then stirred overnight for crystallization. The resulting crystal was recovered by filtration, and then dried to obtain 10.39 g of a crude crystal of 4(5)-chloro-2-cyano-5(4)-(4-methylphenyl)imidazole. The crystal was then analyzed by liquid chromatography (internal standard analysis). As a result, the purity of the product was found to be 74.7%.

EXAMPLE 13

Into a 100-ml four-necked flask equipped with a thermometer, a condenser, an agitator and a dropping funnel were charged 5.83 g of 1-hydroxy-4(5)-(4-methylphenyl)-2-oxyiminomethylimidazole 3-oxide, 35 ml of dimethylformamide and 30 ml of ethyl acetate. To the reaction mixture was then added dropwise 6.0 g of thionyl chloride with stirring while cooling the reaction system to from 20° C. to 30° C. The reaction mixture was then further stirred at room temperature for about one hour. After cooling the reaction system again to about 10° C., 2.7 g of sulfur dichloride was added dropwise to the reaction mixture. The reaction mixture was then stirred for about one hour.

The reaction mixture was then gradually added dropwise to 200 ml of ice water. The resulting organic phase was washed with 200 ml twice. The solvent was then distilled off to obtain 5.96 g of a crude crystal of 4(5)-chloro-2-cyano-5(4)-(4-methylphenyl)imidazole (purity: 68.6%).

EXAMPLE 14

Into a 100-ml four-necked flask equipped with a thermometer, a condenser, an agitator and a dropping funnel were charged 11.65 g of 1-hydroxy-4(5)-(4-methylphenyl)-2-oxyiminomethylimidazole 3-oxide and 35 ml of dimethylformamide. To the reaction mixture was then added dropwise 14.87 g of thionyl chloride with stirring while cooling the reaction system to 25° C. or less. The reaction mixture was then further stirred at room temperature for about one hour. To the reaction mixture was then added dropwise 13.5 g of sulfur monochloride at room temperature. The reaction mixture was then stirred for about 4 hours.

To the reaction mixture was then added 4 ml of methanol. The reaction mixture was then poured into 200 ml of ice water. The resulting crystal was recovered by filtration, dissolved in 200 ml of ethyl acetate, and then filtered to remove insoluble matters. The solvent was then distilled off to obtain 9.97 g of a crude crystal of 4(5)-chloro-2-cyano-5(4)-(4-methylphenyl)imidazole (purity: 64.1%).

EXAMPLE 15

Into a 100-ml four-necked flask equipped with a thermometer, a condenser, an agitator and a dropping funnel were charged 11.65 g of 1-hydroxy-4(5)-(4-methylphenyl)-2-oxyiminomethylimidazole 3-oxide and 35 ml of dimethylformamide. To the reaction mixture was then added dropwise 14.87 g of thionyl chloride with stirring while cooling the reaction system to 25° C. or less. The reaction mixture was then further stirred at room temperature for about one hour. While cooling the reaction system, 0.8 g of methanol was added to the reaction system. Then, 6.75 g of sulfur monochloride was added dropwise to the reaction system. The reaction mixture was then kept at a temperature of from 40° C. to 50° C. for about 3 hours.

To the reaction mixture was then added 1.6 g of methanol. The resulting insoluble matters were then filtered off. The insoluble matters were then washed with 20 ml of ethyl acetate. The mixture of the filtrate and the wash liquid were gradually added dropwise to 200 ml of ice water. The reaction mixture was then stirred for about 4 hours for crystallization. The resulting crystal was recovered by filtration, washed with water, and then dried to obtain 10.74 g of a crude crystal of 4(5)-chloro-2-cyano-5(4)-(4-methylphenyl)imidazole (purity: 67.4%).

EXAMPLE 16

Into a 100-ml four-necked flask equipped with a thermometer, a condenser, an agitator and a dropping funnel were charged 11.65 g of 1-hydroxy-4(5)-(4-methylphenyl)-2-oxyiminomethylimidazole 3-oxide and 35 ml of dimethylformamide. To the reaction mixture was then added dropwise 14.87 g of thionyl chloride with stirring while cooling the reaction system to 25° C. or less. The reaction mixture was then further stirred at room temperature for about one hour.

To the reaction mixture was then added 1.6 g of methanol. The reaction mixture was then poured into 200 ml of ice water, and then extracted with 200 ml of methylene chloride. The solution thus extracted was then washed with 200 ml of water twice. The solvent was then distilled off to obtain 12.54 g of a mixture of 4(5)-chloro-2-cyano-5(4)-(4-methylphenyl)imidazole (purity: 37.0%), 4-chloro-2-cyano-1-hydroxy-5-(4-methylphenyl)imidazole and 2-cyano-1-hydroxy-5-(4-methylphenyl)imidazole. Then, 3.0 g of the mixture was separated by silica gel chromatography to obtain 0.94 g of 4-chloro-2-cyano-1-hydroxy-5-(4-methylphenyl)imidazole (m.p. 212°–215° C.) and a small amount of 2-cyano-1-hydroxy-5-(4-methylphenyl)imidazole (m.p. 224°–228° C.).

The foregoing mixture could produce 4(5)-chloro-2-cyano-5(4)-(4-methylphenyl)imidazole when subjected to the same reaction as the latter stage reaction in Examples 12 to 15.

EXAMPLE 17

Into a four-necked flask equipped with an agitator, an azeotropic dehydrator and a thermometer were charged 8.7 g of 4(5)-chloro-2-cyano-5(4)-(4-methylphenyl)imidazole, 20 ml of ethyl acetate, 6.6 g of potassium carbonate and 6.3 g of dimethylsulfamoyl chloride. The reaction mixture was then heated under reflux for 2 hours. To the reaction system were then added 0.6 g of potassium carbonate and 0.6 g of dimethylsulfamoyl chloride. The reaction mixture was then kept while distilling off ethyl acetate from the reaction system for one hour (yield of the desired compound: 93 mol %). After the completion of the reaction, 20 ml of water and 20 ml of ethyl acetate were poured into the reaction system. The reaction mixture was then stirred at a temperature of from 60° C. to 70° C. for 20 minutes to obtain slurry of the desired compound. The slurry was recovered by filtration, and then dried to obtain 11.7 g of 4-chloro-2-cyano-1-dimethylsulfamoyl-5-(4-methylphenyl)imidazole (purity: 98.2%; yield: 90.5%).

EXAMPLE 18

Into a four-necked flask equipped with an agitator, an azeotropic dehydrator and a thermometer were charged 40.0 g of 4(5)-chloro-2-cyano-5(4)-(4-methylphenyl)imidazole, 80.3 ml of ethyl acetate, 30.6 g of potassium carbonate and 29.2 g of dimethylsulfamoyl chloride. The reaction mixture was then heated under reflux for 2 hours. To the reaction system were then added 5.1 g of potassium carbonate and 5.3 g of dimethylsulfamoyl chloride. After the addition, to the reaction system were further added 2.6 g of potassium carbonate and 2.7 g of dimethylsulfamoyl chloride. That is, potassium carbonate and dimethylsulfamoyl chloride were added batchwise two times in a total amount of 7.7 g and 8.0 g, respectively. After the batchwise addition, the mixture was reacted while distilling off ethyl acetate from the reaction system for 1.5 hours (yield of the desired compound: 90 mol %). After the completion of the reaction, 80 ml of water and 80 ml of ethyl acetate were poured into the reaction system to obtain a slurry. The slurry was recovered by filtration, and then dried to obtain 55.8 g of 4-chloro-2-cyano-1-dimethylsulfamoyl-5-(4-methylphenyl)imidazole (purity: 99.0%; yield: 92.5%).

EXAMPLE 19

Into a four-necked flask equipped with an agitator, an azeotropic dehydrator and a thermometer were charged 5.0 g of 4(5)-chloro-2-cyano-4-(methylphenyl)imidazole, 10 ml of methyl ethyl ketone, 3.6 g of potassium carbonate and 3.4 g of dimethylsulfamoyl chloride. The reaction mixture was then heated under reflux for 2 hours. To the reaction system were then added 0.3 g of potassium carbonate and 0.3 g of dimethylsulfamoyl chloride. After the addition, to the reaction system were further added 0.1 g of potassium carbonate and 0.1 g of dimethylsulfamoyl chloride. That is, potassium carbonate and dimethylsulfamoyl chloride were added batchwise two times in a total amount of 0.4 g and 0.4 g, respectively. After the batchwise addition, the reaction mixture was kept while distilling off methyl ethyl ketone from the reaction system for 1.5 hours (yield of the desired compound: 95 mol %). After the completion of the reaction, 30 ml of water was poured into the reaction system to obtain a slurry. The slurry was recovered by filtration, and then dried to obtain 6.8 g of 4-chloro-2-cyano-1-dimethylsulfamoyl-5-(4-methylphenyl)imidazole (purity: 99.0%; yield: 95.0%).

While the invention has been described in detail and with reference to specific embodiments thereof, it will be apparent to one skilled in the art that various changes and modifications can be made therein without departing from the spirit and scope thereof.

What is claimed is:

1. A process for producing 1-substituted-2-cyanoimidazole compounds, which comprises (1) undergoing a reaction of a compound represented by the following formula (IV), hydroxylamine or a mineral acid salt thereof, and glyoxal or glyoxime to produce a compound represented by the following formula (III):

wherein $A^1$ represents a hydrogen atom, a chlorine atom or a bromine atom; $A^2$ represents a chlorine atom or a bromine atom; X represents an unsubstituted phenyl group, a phenyl group substituted by at least one substituent selected from the group consisting of a halogen atom, a $C_{1-3}$ alkyl group and a $C_{1-3}$ alkoxy group, an unsubstituted alkyl group or an alkyl group substituted by at least one substituent selected from the group consisting of a halogen atom, a phenyl group and a $C_{1-3}$ alkoxy group; and Z represents an oxygen atom or a hydroxyimino group:

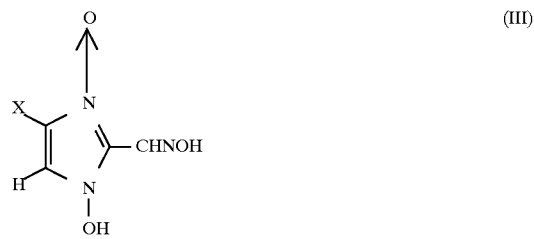

wherein X has the same meaning as defined above, (2) undergoing a reaction of the compound represented by formula (III) with thionyl chloride or thionyl bromide in the presence of N,N-dialkylamide to produce a reaction mixture, and then undergoing a reaction of the produced reaction mixture with sulfur chloride to produce a 2-cyanoimidazole compound represented by the following formula (II):

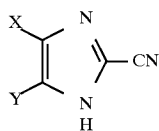

(II)

wherein X has the same meaning as defined above; and Y represents a chlorine atom or a bromine atom, and (3) undergoing a sulfamoylation reaction and an isomerization reaction of the 2-cyanoimidazole compound represented by formula (II) and a compound represented by the following formula (V) in the presence of at least one base selected from carbonates of alkali metals and bicarbonates of alkali metals and a polar solvent to produce a 1-substituted-2-cyanoimidazole compound represented by the following formula (I-b):

(V)

wherein Hal represents a halogen atom; and $R^1$ and $R^2$ each represents an alkyl group:

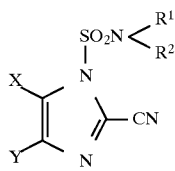

(I-b)

wherein $R^1$, $R^2$, X and Y each has the same meaning as defined above.

2. A process for producing a product consisting essentially of a 1-substituted-2-cyanoimidazole compound represented by the following formula (I-b), which comprises undergoing a sulfamoylation reaction and an isomerization reaction of a compound represented by the following formula (II) and a compound represented by the following formula (V) in the presence of at least one base selected from carbonates of alkali metals and bicarbonates of alkali metals and 1 to 3 l per kg of the compound represented by formula (II) of a polar solvent:

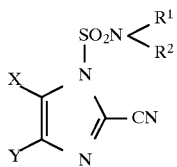

(I-b)

wherein $R^1$ and $R^2$ each represents an alkyl group; X represents an unsubstituted phenyl group, a phenyl group substituted by at least one substituent selected from the group consisting of a halogen atom, a $C_{1-3}$ alkyl group and a $C_{1-3}$ alkoxy group, an unsubstituted alkyl group or an alkyl group substituted by at least one substituent selected from the group consisting of a halogen atom, a phenyl group and a $C_{1-3}$ alkoxy group; and Y represents a chlorine atom or a bromine atom;

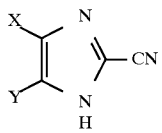

(II)

wherein X and Y each has the same meaning as defined above;

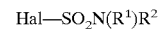

(V)

wherein Hal represents a halogen atom; and $R^1$ and $R^2$ each has the same meaning as defined above.

3. The process according to claim 2, wherein the polar solvent is methyl ethyl ketone or ethyl acetate.

4. The process according to claim 2, wherein the solvent is gradually distilled off during the sulfamoylation reaction and the isomerization reaction.

5. The process according to claim 2, wherein the reactions are carried out at a temperature of from 20° C. to 110° C.

* * * * *